(12) United States Patent
Watanabe et al.

(10) Patent No.: US 9,962,335 B2
(45) Date of Patent: May 8, 2018

(54) METHOD OF MANUFACTURING ENTERIC SOFT CAPSULE

(71) Applicant: FUJI CAPSULE CO., LTD., Shizuoka (JP)

(72) Inventors: Kazuhiko Watanabe, Shizuoka (JP); Hiroaki Hasegawa, Shizuoka (JP); Nahonori Inaba, Shizuoka (JP); Yoshiyuki Shimokawa, Shizuoka (JP); Kenji Kato, Shizuoka (JP)

(73) Assignee: FUJI CAPSULE CO., LTD., Shizuoka (JP)

( * ) Notice: Subject to any disclaimer, the term of this patent is extended or adjusted under 35 U.S.C. 154(b) by 0 days. days.

(21) Appl. No.: 15/305,670

(22) PCT Filed: Oct. 6, 2015

(86) PCT No.: PCT/JP2015/005083
§ 371 (c)(1),
(2) Date: Oct. 21, 2016

(87) PCT Pub. No.: WO2016/056230
PCT Pub. Date: Apr. 14, 2016

(65) Prior Publication Data
US 2017/0209384 A1    Jul. 27, 2017

(30) Foreign Application Priority Data

Oct. 6, 2014 (JP) ................................ 2014-205991

(51) Int. Cl.
*A61K 9/50* (2006.01)
*A61K 9/48* (2006.01)
*A61K 31/202* (2006.01)

(52) U.S. Cl.
CPC .......... *A61K 9/4833* (2013.01); *A61K 9/4816* (2013.01); *A61K 9/4825* (2013.01); *A61K 31/202* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,254,294 A | * | 10/1993 | Wunderlich | A61K 9/4833 264/4 |
| 6,410,050 B1 | * | 6/2002 | Yang | A61K 9/4816 424/400 |
| 6,627,236 B1 | * | 9/2003 | Barbeau | A23C 9/137 426/103 |
| 7,041,315 B2 | * | 5/2006 | Scott | A61K 8/0216 424/451 |
| 7,112,292 B2 | * | 9/2006 | Nakajima | A61J 3/07 264/4 |
| 7,309,499 B2 | * | 12/2007 | Yang | A61K 9/4816 424/451 |
| 2005/0019295 A1 | * | 1/2005 | Ballard | A61K 8/0208 424/70.13 |

FOREIGN PATENT DOCUMENTS

| | | |
|---|---|---|
| JP | 2006-505542 A | 2/2006 |
| JP | 2009-521269 | 6/2009 |
| JP | 2009-185022 | 8/2009 |
| JP | 2010-047548 | 3/2010 |

OTHER PUBLICATIONS

International Preliminary Report on Patentabililty, PCT/JP2015/005083 [WIPO] dated Apr. 20, 2017.

* cited by examiner

*Primary Examiner* — Kara B Boyle
(74) *Attorney, Agent, or Firm* — Edwin S. Flores; Daniel J. Chalker; Chalker Flores, LLP

(57) ABSTRACT

An object is to provide a method of manufacturing a soft capsule that is enteric and excellent in formulation properties. An enteric soft capsule is manufactured by the following steps (a) and (b): (a) preparing an enteric capsule shell liquid comprising gelatin and low methoxyl pectin having a degree of amidation of 5 to 25%, and (b) encapsulating capsule fills using the enteric capsule shell liquid prepared in the step (a) by stamping. Preferably, the jelly strength of the gelatin is 160 to 300 Bloom, the degree of esterification of the low methoxy pectin is 20 to 40%, and the enteric capsule shell liquid comprises 30 to 35 parts by mass of the low methoxy pectin per 100 parts by mass of the gelatin.

20 Claims, No Drawings

METHOD OF MANUFACTURING ENTERIC SOFT CAPSULE

CROSS REFERENCE TO RELATED APPLICATIONS

This application is the National Stage of International Application No. PCT/JP2015/005083, filed on Oct. 6, 2015 claiming the priority of JP 2014-205991, filed on Oct. 6, 2014, the content of each of which is incorporated by reference herein.

TECHNICAL FIELD

The present invention relates to a method of manufacturing an enteric soft capsule, and more particularly to a method of manufacturing an enteric soft capsule, comprising the following steps (a) and (b): (a) preparing an enteric capsule shell liquid comprising gelatin and low methoxy pectin having a degree of amidation of 5 to 25%, and (b) encapsulating capsule fills using the enteric capsule shell liquid prepared in the step (a) by stamping.

BACKGROUND ART

A variety of conventional capsules containing various active ingredients have been reported. Widely used materials of shells of these capsules include gelatin and agar. Since shells made of materials such as gelatin and agar disintegrate in the acidic environment of the stomach, it was not possible to use acid-labile substances as active ingredients.

Enteric capsules have been recently developed for this reason. Enteric capsules are capsules whose shells have acid resistance, therefore do not disintegrate in the stomach, but disintegrate in the intestines to release the capsule fills. These enteric capsules are used not only to encapsulate acid-labile substances as active ingredients, but also to encapsulate substances to be released slowly for effects sustained for a long period of time and substances that cause bad breath and flavor reversion when digested in the stomach, such as garlic and a fish oil.

Methods of manufacturing enteric capsules proposed so far include a method comprising (a) preparing a solution comprising a film-forming, water-soluble polymer and an acid-insoluble polymer and mixing with appropriate plasticizers to form a gel mass; (b) casting the gel mass into films or ribbons using heat-controlled drums or surfaces; and (c) forming a soft capsule using rotary die technology (see Patent Document 1).

Also proposed is a method of manufacturing an enteric, sustained-release soft capsule, comprising manufacturing a soft capsule material mixture obtained by homogeneously mixing and kneading gelatin, polyol as a plasticizer, an alkali metal salt, water, and a polysaccharide such as carrageenan, agar, or locust bean gum at a concentration of 6 to 40% by mass; and encapsulating at least one selected from garlic, a fish oil, propolis, an enteric bacterium, and a protein agent with the soft capsule material mixture (see Patent Document 2). However, since 2 or more polysaccharides are necessary and an alkali metal salt is necessary at the time of mixing and kneading, gelation with 2 polysaccharides is already promoted at the time of the capsule formation, causing a problem of very poor formability (very poor adhesiveness).

Further proposed is a method of manufacturing an enteric soft capsule, comprising a preparation step of preparing a capsule shell liquid comprising gelatin, water, a plasticizer, and 10 to 30 parts by weight of low methoxyl pectin having a degree of esterification of 20 to 40% per 100 parts by weight of gelatin; and a capsule-forming step of forming a soft capsule in which fill materials are packed into a capsule shell formed from the capsule shell liquid with a rotary die capsule-forming apparatus; wherein the capsule shell liquid comprises no salts comprising a polyvalent metal ion that gelates low methoxyl pectin and the method comprises no step of immersing the formed soft capsule in a gelation solution comprising the polyvalent metal ion (see Patent Document 3).

PRIOR ART DOCUMENTS

Patent Documents

Patent Document 1: Japanese unexamined Patent Application Publication (Translation of PCT Application) No. 2006-505542
Patent Document 2: Japanese unexamined Patent Application Publication No. 2009-185022
Patent Document 3: Japanese unexamined Patent Application Publication No. 2010-047548

SUMMARY OF THE INVENTION

Object to be Solved by the Invention

An object of the present invention is to provide a method of manufacturing a soft capsule that is enteric and excellent in formulation properties.

Means to Solve the Object

The present inventors focused on the degree of amidation of pectin used in a capsule shell in the manufacturing of enteric soft capsules. The present inventors tried various types of pectin having different degrees of amidation in capsule shell materials and found that soft capsules that are enteric and excellent in formulation properties can be manufactured by using low methoxy pectin having a degree of amidation of 5 to 25%, thereby completing the present invention.

Accordingly, the present invention is as disclosed below.
(1) A method of manufacturing an enteric soft capsule, comprising the following steps (a) and (b): (a) preparing an enteric capsule shell liquid comprising gelatin and low methoxy pectin having a degree of amidation of 5 to 25%, and (b) encapsulating capsule fills using the enteric capsule shell liquid prepared in the step (a) by stamping.
(2) The method of manufacturing an enteric soft capsule according to (1) above, wherein a jelly strength of the gelatin is 160 to 300 Bloom.
(3) The method of manufacturing an enteric soft capsule according to (1) or (2) above, wherein a degree of esterification of the low methoxy pectin is 20 to 40%
(4) The method of manufacturing an enteric soft capsule according to any one of (1) to (3) above, wherein the enteric capsule shell liquid comprises 30 to 35 parts by mass of the low methoxy pectin per 100 parts by mass of the gelatin.
(5) The method of manufacturing an enteric soft capsule according to any one of (1) to (4) above, wherein the low methoxy pectin is dispersed in glycerin and subsequently dissolved in hot water, then gelatin is added and dissolved, and the mixture is filtered and degassed under reduced pressure.

(6) The method of manufacturing an enteric soft capsule according to any one of (1) to (5) above, wherein the encapsulation is performed such that a thickness of the enteric capsule shell is 0.3 to 1.2 mm.

Effects of the Invention

Enteric soft capsules manufactured by a method of manufacturing an enteric soft capsule according to the present invention are enteric and excellent in formulation properties. Therefore, they can be stored for a long period of time and encapsulate fill materials containing an acid-labile substance. In addition, they can prevent bad breath and flavor reversion after administering fill materials containing a substance that causes bad breath or flavor reversion when digested in the stomach, such as garlic and a fish oil, encapsulated therein.

MODE OF CARRYING OUT THE INVENTION

A method of manufacturing an enteric soft capsule according to the present invention is not particularly limited as long as it is a method of manufacturing an enteric soft capsule, comprising the following steps (a) and (b): (a) preparing an enteric capsule shell liquid comprising gelatin and low methoxy pectin having a degree of amidation of 5 to 25%, and (b) encapsulating capsule fills with the enteric capsule shell liquid prepared in the step (a) by stamping. "Enteric" refers to the property of being dissolved in intestines, but not dissolved in the stomach.

Gelatin in the present invention is not particularly limited, but examples include gelatin having a jelly strength of 160 to 300 Bloom, and preferably 200 to 300 Bloom. Moreover, mixtures of 2 or more gelatins different in jelly strength can be used. For example, 2 gelatins having jelly strengths of 200 Bloom and 300 Bloom can be mixed to adjust the jelly strength.

In the present invention, low methoxy pectin (LM pectin) refers to pectin having a degree of esterification (DE) of less than 50% and such a degree of esterification is preferably 20 to 40%, more preferably 22 to 38%, and further preferably 22 to 32%. The degree of esterification means percentage of methyl esterified galacturonic acid to total galacturonic acid and is the value (%) calculated by dividing the number of methyl esterified galacturonic acid by the number of total galacturonic acid and multiplying the obtained value by 100.

In the present invention, degree of amidation (DA) means percentage of amidated galacturonic acid to total galacturonic acid and is the value (%) calculated by dividing the number of amidated galacturonic acid by the number of total galacturonic acid and multiplying the obtained value by 100. Examples of the degree of amidation of the aforementioned low methoxy pectin are 5 to 25%, preferably 6 to 23%, and more preferably 12 to 23%.

A method of preparing an enteric capsule shell liquid according to the present invention is not particularly limited and examples include a method comprising dissolving low methoxy pectin having a degree of amidation of 5 to 25% in water then adding gelatin to the mixture and dissolving the gelatin. In view of quality control such as securing of the homogeneity of the shell solution, the prevention of weakening of capsule shells, and the prevention of deformation and poor adhesiveness of capsules, it is preferred to dissolve the aforementioned low methoxy pectin in hot water after dispersing it in a plasticizer such as glycerin; to filter the prepared enteric capsule shell liquid through a mesh with 0.5 mm or smaller aperture, and preferably 0.3 mm or smaller to remove undissolved materials such as lumps of undissolved powder and foreign substances; and to further degas the shell liquid under vacuum when the shell solution is liquid.

In the present invention, a method of encapsulating capsule fills by stamping is not particularly limited as long as it is a method comprising: feeding 2 sheets of gelatin formed by spreading the capsule shell liquid to a pair of dies for the capsule formation, injecting a fill material liquid between the 2 sheets, and forming capsules while filling the fill materials by stamping. Examples include a method comprising encapsulating capsule fills by the rotary die process, in which dies are cylindrical, or the plate process, in which dies are planar plates. Materials of the aforementioned dies are not particularly limited, but preferred examples include a metal "die". The aforementioned rotary die process and the plate process can be respectively conducted using a rotary die soft capsule-manufacturing apparatus and a plate soft capsule-manufacturing apparatus commercially available. In stamping, a seam is formed during the pressing in the formation. If the adhesiveness (enclosure and stickiness) of such seam is low, the capsule disintegrates easily. However, enteric soft capsules manufactured according to the present invention have high adhesiveness at their seams because of low methoxy pectin having a degree of amidation of 5 to 25% contained in their shells and, as a result, can be stored stably for a long period of time.

In the present invention, capsule fills are not particularly limited and can be a solid or a liquid and examples include a pharmaceutical ingredient, a supplement ingredient, and a health food ingredient. Specific examples include a substance that causes bad breath or flavor reversion when digested in the stomach such as a fish oil, garlic, vitamin B1, or so-called egg-yolk oil (a traditional health food material that is a brown to black liquid obtained by heating egg yolk over a low flame with stirring in an iron pan or the like for a long time); an acid-labile enteric bacterium representative by a lactic acid bacterium such as *Streptococcus faecium*, *Lactobacillus lactis* subsp. *lactis*, *Lactobacillus helveticus*, *Lactobacillus acidophilus*, or *Lactobacillus casei*; a bifidobacterium such as *Bifidobacterium longum* and *Bifidobacterium bifidum*; an ingredient stimulating to the stomach such as a red pepper material or capsaicin; a chalybeate such as ferrous fumarate or dried ferrous sulfate; and an agent desired to be released slowly to have an effect sustained for a long period of time such as an antifebrile, a pain-killer, an antiphlogistic, an antitumor agent, or an antimicrobial agent.

Besides the aforementioned ingredients, the aforementioned capsule fills can contain, as needed, an oil or fat such as hydrogenated oil, medium chain triglyceride (MCT), EPA, DHA, shark liver oil, or cod-liver oil; an additive that can be used to adjust the surface activity such as lecithin, polyglycerol ester of fatty acid, or alcohol; buffer; water; a gelling agent such as gelatin or carrageenan; a pH regulator; porous fine particle powder such as gas phase process silica; a tasting agent such as a sweetener; a fragrance; a solubilizer; a viscosity modifier; an antioxidant represented by vitamin E, BHT, BHA.

The content of the low methoxy pectin relative to gelatin in the enteric capsule shell liquid of the present invention is not particularly limited, but the content of the low methoxy pectin is preferably 20 to 40 parts by mass, more preferably 30 to 35 parts by mass, and further preferably 31 to 33 parts by mass per 100 parts by mass of the gelatin.

In the present invention, encapsulation of capsule fills is preferably conducted such that the thickness of the shell is 0.3 to 1.2 mm and more preferably conducted such that the thickness is 0.4 to 1.0 mm.

The enteric capsule shell liquid in the present invention can contain, as needed, a plasticizer such as glycerin, a PH regulator such as sodium phosphate, a chelating agent such as trisodium citrate or sodium metaphosphate, a gelling enhancer such as calcium lactate or potassium chloride, a surfactant such as polyglycerol ester of fatty acid or lecithin, a sweetener, a fragrance, a preservative, or a colorant. However, no gelling enhancer is preferably blended in the shell liquid for formability and adhesiveness of the capsule. A gelling enhancer can be included at any time point (before, during, or after drying) after the formation of capsules by a method such as immersing treatment or spray coating.

EXAMPLES

Example 1

[Disintegration Test]
(Production of Soft Capsule)

24 parts by mass of pectin (DE30, DA17) was dispersed in 30 parts by mass of glycerin and dissolved in hot water (80° C.). 60 parts by mass of gelatin (300 Bloom) and 16 parts by mass of gelatin (200 Bloom) were further added to the solution and dissolved at 70° C. The solution was filtered through 100 mesh (aperture 0.15 mm) and subsequently degassed under reduced pressure to prepare a capsule shell liquid according to the present invention. A control shell liquid was also prepared by dissolving 30 parts by mass of glycerin in hot water at 80° C., adding 100 parts by mass of gelatin (200 Bloom), dissolving the gelatin at 70° C., filtering the solution through 100 mesh (aperture 0.15 mm), and subsequently degassing the filtrate under reduced pressure. Each of the capsule shell liquid was fluid at 60° C. and in a condition that does not cause a problem in use in a rotary apparatus.

Then, using a rotary die soft capsule manufacturing apparatus (manufactured by Fuji Capsule Co., Ltd.), 250 mg of capsule fills (a fish oil containing DHA and EPA) was encapsulated with shell sheets having a thickness of about 0.8 mm formed by spreading the aforementioned capsule shell liquid according to the present invention or the control shell liquid. The resulting capsules were subsequently dried with turning under dehumidification environment at 30° C. and 35% in humidity for 12 hours to manufacture Oval-5 soft capsules. After the drying, the resulting capsules had a shell thickness of 0.5 mm and an excellent adhesion rate (thickness of the thinnest part of adherend/average thickness of the shell, measurement by viewing) of 85%.

(Result)

Soft capsules manufactured from the capsule shell liquid according to the present invention and soft capsules manufactured from the control shell liquid were administered and smell of breath was examined 60 minutes later. As a result, fishy smell was not noticed when soft capsules manufactured from the capsule shell liquid according to the present invention were administered but noticed when soft capsules manufactured from the control shell solution were administered.

Example 2

[Formulation and Enteric Properties Test 1]
(Production of Soft Capsule)

31.5 parts by mass of each type of pectin set forth in Table 1 below was dispersed in 40 parts by mass of glycerin and dissolved in hot water (80° C.). 79 parts by mass of gelatin (300 Bloom) and 21 parts by mass of gelatin (200 Bloom) were further added and dissolved at 70° C. The mixture was filtered through 60 mesh (aperture 0.25 mm) and subsequently degassed under reduced pressure to prepare the capsule shell liquid. In the table, DE indicates the degree of esterification (%) of each type of pectin and DA indicates the degree of amidation (%) of each type of pectin.

TABLE 1

| Type of pectin | DE | DA |
| --- | --- | --- |
| Pectin-1 | 31-38 | 12-18 |
| Pectin-2 | 26-34 | 16-19 |
| Pectin-3 | 30-35 | 6-12 |
| Pectin-4 | 22-27 | 20-23 |
| Pectin-5 | 33-38 | 0 |

Then, using a plate soft capsule manufacturing apparatus (manufactured by Fuji Capsule Co., Ltd.), medium chain triglycerides (MCT: COCONARD MT: manufactured by Kao Corporation) as capsule fills was encapsulated with shell sheets having a thickness of about 0.8 mm obtained by spreading the aforementioned capsule shell liquid at an average of 0.45 mL per capsule. The resulting capsules were subsequently allowed to stand for drying at 25° C. without controlling humidity for 18 hours to manufacture Oval-5 soft capsules. Soft capsules manufactured with shell liquid containing Pectin-1 to Pectin-4 were respectively designated as Example Products 1 to 4 and a soft capsule manufactured with Pectin 5 were designated as Comparison Product. After the drying, the obtained soft capsules had a shell thickness of 0.5 mm and an adhesion rate (thickness of the thinnest part of adherend/average thickness of the shell, measurement by viewing) of 60%, which is excellent for capsules manufactured by the plate process.

The obtained soft capsules were evaluated for their formulation properties and enteric properties. For the evaluation of formulation properties, the fluidity of the shell liquid (if there is an trouble in injecting the solutions into the apparatus) was examined and rated as ⊙ when there was no trouble at all, ○ when there was almost no trouble, Δ when there was a slight trouble, and x when there was an unacceptable trouble. The adhesiveness (state of adhesion at the join between the sheets) at the time of the capsule formation was also examined and rated as ⊙ when it was very good, ○ when it was good, Δ when it was slightly bad, and x when it was bad.

For evaluation of enteric properties, the disintegration tests described below were conducted and results of the observation after 120 minutes of the disintegration test in 1st Fluid (37° C.) were rated as ○ when there was no disintegration and x when there was disintegration; and results of the observation after 30 minutes of the disintegration test in 2nd Fluid were rated as ○ when all capsules were disintegrated and x when not all capsules were disintegrated.

The disintegration tests of the manufactured soft capsules were conducted by methods modified from the methods described in literature (Guidebook to The Japanese Pharmacopoeia 16th edition, Tokyo Hirokawa Shoten, publication B589 (2011)). The disintegration tester NT-40H (manufactured by Toyama Sangyo Co., Ltd.) was used. A test using the reagent "1st Fluid for disintegration test/1st Fluid for dissolution test" (pH 1.2) manufactured by Kanto Chemical Co., Inc. and a test using the reagent "2nd Fluid for disintegration test" (pH 6.8) manufactured by Kanto Chemical Co., Inc. were conducted for 18 capsules each without (Example Products 1 to 4) and with (only Example Product 2) a disk. Capsules were considered disintegrated when they were broken or their shells were open or damaged.

(Result)

The results of the examination on formulation properties and enteric properties are shown in Table 2. As shown in Table 2, all of Example products 1 to 4 had good formulation properties. As to enteric properties, Example products 1 to 4 (without a disk) exhibited no disintegration for all 18 soft capsules after 120 minutes of the disintegration test in 1st Fluid and exhibited disintegration from after 5 minutes of the test in 2nd Fluid for disintegration test using new capsules and all soft capsules were disintegrated after 30 minutes of the test. Example product 2 (with a disk) exhibited no disintegration for all 18 soft capsules after 120 minutes of the disintegration test in 1st Fluid and exhibited openings from after 3 minutes of the test using 2nd Fluid for disintegration test using new capsules and all 18 soft capsules disintegrated after 30 minutes of the test.

Thus, it was revealed that soft capsules excellent in formulation properties and enteric properties can be manufactured by manufacturing soft capsules by stamping using an enteric capsule shell solution comprising gelatin and low methoxy pectin having a degree of amidation of 5 to 25%.

TABLE 2

| Type of pectin | Evaluation of formulation properties | | Evaluation of enteric properties | |
|---|---|---|---|---|
| | Fluidity of shell liquid | Adhe- siveness | 1st Fluid | 2nd Fluid |
| Example product 1 | Pectin-1 | ⊙ | ○ | ○ | ○ |
| Example product 2 | Pectin-2 | ⊙ | ○ | ○ | ○ |
| Example product 3 | Pectin-3 | ○ | ○ | ○ | ○ |
| Example product 4 | Pectin-4 | ⊙ | ⊙ | ○ | ○ |
| Comparison product | Pectin-5 | Δ | Δ | X | — |

Example 3

[Formulation and Enteric Properties Test 2]

(Production of Soft Capsule)

20 parts by mass each of Pectin-1, Pectin-2, and Pectin-4 set forth in Table 1 above were dispersed in 40 parts by mass of glycerin and dissolved in hot water (80° C.). 79 parts by mass of gelatin (300 Bloom) and 21 parts by mass of gelatin (200 Bloom) were further added and dissolved at 70° C. The solution was filtered through 60 mesh (aperture 0.25 mm) and subsequently degassed under reduced pressure to prepare a capsule shell liquid.

Then, using a plate soft capsule manufacturing apparatus (manufactured by Fuji Capsule Co., Ltd.), Oval-5 soft capsules encapsulating the MCT contents were manufactured in the same method as described above. Soft capsules manufactured using Pectin-1, Pectin-2, and Pectin-4 were respectively designated as Example Products 5 to 7.

The obtained soft capsules were evaluated for formulation properties and enteric properties as described above. The results are shown in Table 3.

TABLE 3

| Type of pectin | Evaluation of formulation properties | | Evaluation of enteric properties | |
|---|---|---|---|---|
| | Fluidity of shell liquid | Adhe- siveness | 1st Fluid | 2nd Fluid |
| Example product 5 | Pectin-1 | ○ | Δ | ○ | ○ |
| Example product 6 | Pectin-2 | ?? | Δ | ○ | ○ |
| Example product 7 | Pectin-4 | ○ | Δ | ○ | ○ |

(Result)

Example products 5 to 7 were slightly inferior to Example products 1, 2, and 4 on the fluidity of shell in formulation properties but had almost no trouble and slightly inferior to Example products 1 to 4 on adhesiveness. As to enteric properties, they were as good as Example products 1 to 4.

INDUSTRIAL APPLICABILITY

The enteric soft capsules of the present invention are excellent in enteric properties and formulation properties and available in the fields of pharmaceuticals, supplements, and health food.

The invention claimed is:

1. A method of manufacturing an enteric soft capsule, comprising the following steps (a) and (b):
   (a) preparing an enteric capsule shell liquid comprising gelatin and low methoxy pectin having a degree of amidation of 5 to 25%, and
   (b) encapsulating capsule fills using the enteric capsule shell liquid prepared in the step (a) by stamping.

2. The method of manufacturing an enteric soft capsule according to claim 1, wherein a jelly strength of the gelatin is 160 to 300 Bloom.

3. The method of manufacturing an enteric soft capsule according to claim 1, wherein a degree of esterification of the low methoxy pectin is 20 to 40%.

4. The method of manufacturing an enteric soft capsule according to claim 1, wherein the enteric capsule shell liquid comprises 30 to 35 parts by mass of the low methoxy pectin per 100 parts by mass of the gelatin.

5. The method of manufacturing an enteric soft capsule according to claim 1, wherein the low methoxy pectin is dispersed in glycerin and subsequently dissolved in hot water, then gelatin is added and dissolved, and the mixture is filtered and degassed under reduced pressure.

6. The method of manufacturing an enteric soft capsule according to claim 1, wherein the encapsulation is performed such that a thickness of the enteric capsule shell is 0.3 to 1.2 mm.

7. The method of manufacturing an enteric soft capsule according to claim 2, wherein a degree of esterification of the low methoxy pectin is 20 to 40%.

8. The method of manufacturing an enteric soft capsule according to claim 2, wherein the enteric capsule shell liquid comprises 30 to 35 parts by mass of the low methoxy pectin per 100 parts by mass of the gelatin.

9. The method of manufacturing an enteric soft capsule according to claim 3, wherein the enteric capsule shell liquid comprises 30 to 35 parts by mass of the low methoxy pectin per 100 parts by mass of the gelatin.

10. The method of manufacturing an enteric soft capsule according to claim 7, wherein the enteric capsule shell liquid comprises 30 to 35 parts by mass of the low methoxy pectin per 100 parts by mass of the gelatin.

11. The method of manufacturing an enteric soft capsule according to claim 2, wherein the low methoxy pectin is dispersed in glycerin and subsequently dissolved in hot water, then gelatin is added and dissolved, and the mixture is filtered and degassed under reduced pressure.

12. The method of manufacturing an enteric soft capsule according to claim 3, wherein the low methoxy pectin is dispersed in glycerin and subsequently dissolved in hot water, then gelatin is added and dissolved, and the mixture is filtered and degassed under reduced pressure.

13. The method of manufacturing an enteric soft capsule according to claim 4, wherein the low methoxy pectin is dispersed in glycerin and subsequently dissolved in hot water, then gelatin is added and dissolved, and the mixture is filtered and degassed under reduced pressure.

14. The method of manufacturing an enteric soft capsule according to claim 7, wherein the low methoxy pectin is dispersed in glycerin and subsequently dissolved in hot water, then gelatin is added and dissolved, and the mixture is filtered and degassed under reduced pressure.

15. The method of manufacturing an enteric soft capsule according to claim 8, wherein the low methoxy pectin is dispersed in glycerin and subsequently dissolved in hot water, then gelatin is added and dissolved, and the mixture is filtered and degassed under reduced pressure.

16. The method of manufacturing an enteric soft capsule according to claim 9, wherein the low methoxy pectin is dispersed in glycerin and subsequently dissolved in hot water, then gelatin is added and dissolved, and the mixture is filtered and degassed under reduced pressure.

17. The method of manufacturing an enteric soft capsule according to claim 10, wherein the low methoxy pectin is dispersed in glycerin and subsequently dissolved in hot water, then gelatin is added and dissolved, and the mixture is filtered and degassed under reduced pressure.

18. The method of manufacturing an enteric soft capsule according to claim 2, wherein the encapsulation is performed such that a thickness of the enteric capsule shell is 0.3 to 1.2 mm.

19. The method of manufacturing an enteric soft capsule according to claim 3, wherein the encapsulation is performed such that a thickness of the enteric capsule shell is 0.3 to 1.2 mm.

20. The method of manufacturing an enteric soft capsule according to claim 4, wherein the encapsulation is performed such that a thickness of the enteric capsule shell is 0.3 to 1.2 mm.

* * * * *